(12) United States Patent
Schulz et al.

(10) Patent No.: US 7,418,859 B2
(45) Date of Patent: Sep. 2, 2008

(54) DEVICE FOR MEASURING A VOLUME FLOW WITH INDUCTIVE COUPLING

(75) Inventors: Volkmar Schulz, Stollberg (DE); Henning Gerder, Lübeck (DE)

(73) Assignee: Dräger Medical AG & Co. KG, Lübeck (DE)

( * ) Notice: Subject to any disclaimer, the term of this patent is extended or adjusted under 35 U.S.C. 154(b) by 0 days.

(21) Appl. No.: 11/352,886

(22) Filed: Feb. 13, 2006

(65) Prior Publication Data

US 2006/0191354 A1    Aug. 31, 2006

(30) Foreign Application Priority Data

Feb. 25, 2005    (DE) ................... 10 2005 008 698

(51) Int. Cl.
*G01F 1/69*    (2006.01)
*G01F 1/684*    (2006.01)
*A61M 16/00*    (2006.01)
*A61B 5/087*    (2006.01)

(52) U.S. Cl. ............... 73/204.25; 73/204.27; 73/204.17; 128/200.24; 600/533; 600/538; 600/537

(58) Field of Classification Search ............ 128/200.24, 128/204.17, 204.22, 204.23, 207.14; 73/861.08, 73/861.11, 861.01, 861.16, 204.16–204.19, 73/204.23, 204.25, 204.27; 600/529, 533, 600/538, 532, 537
See application file for complete search history.

(56) References Cited

U.S. PATENT DOCUMENTS 4,467,658 A * 8/1984 Dube et al.

4,576,050 A * 3/1986 Lambert .................. 73/861.95
4,934,189 A * 6/1990 Tanimoto et al. ......... 73/204.14
5,131,399 A * 7/1992 Sciarra ...................... 600/484

(Continued)

FOREIGN PATENT DOCUMENTS

DE    196 54 990 A1    6/1998

(Continued)

OTHER PUBLICATIONS

M. Paksuniemi, H. Sorvoja, E. Alasaarela, R. Myllylä. Wireless sensor and data transmission needs and technologies for patient monitoring in the operating room and intensive care unit. Proceedings of the 2005 IEEE Engineering in Medicine and Biology 27th Annual Conference. Sep. 1-4, 2005. Accessed online on Feb. 18, 2008.*

*Primary Examiner*—Edward Lefkowitz
*Assistant Examiner*—Punam Patel
(74) *Attorney, Agent, or Firm*—McGlew & Tuttle, P.C.

(57) ABSTRACT

A device for measuring a volume flow, especially a tidal volume flow sensor, with a flow channel (1) and with a sensor element (6) arranged within the flow channel (1), is shown and described. The task of providing such a device, in which the sensor signal, which is generated by sensor elements arranged in the flow channel, remains as free as possible from distortions during the transmission to an evaluating unit, is accomplished by providing an internal circuit (3), which is arranged within the flow channel (1) and includes the sensor element (6). An external circuit (7) is arranged outside the flow channel (1). The external circuit (7) is designed for contactless, inductive coupling with the internal circuit (3) for supplying same with energy and for reading.

22 Claims, 6 Drawing Sheets

U.S. PATENT DOCUMENTS

| | | | |
|---|---|---|---|
| 5,339,051 A * | 8/1994 | Koehler et al. | 331/65 |
| 5,462,525 A * | 10/1995 | Srisathapat et al. | 604/67 |
| 6,206,835 B1 * | 3/2001 | Spillman et al. | 600/485 |
| 6,274,951 B1 * | 8/2001 | Saikalis et al. | 307/91 |
| 6,357,438 B1 * | 3/2002 | Hansen | 128/204.18 |
| 6,442,413 B1 * | 8/2002 | Silver | 600/345 |
| 6,453,754 B1 * | 9/2002 | Florin | 73/861.11 |
| 6,615,667 B2 * | 9/2003 | Smith | 73/719 |
| 6,736,980 B2 * | 5/2004 | Moscaritolo | 210/741 |
| 6,856,291 B2 * | 2/2005 | Mickle et al. | 343/701 |
| 2001/0006342 A1 * | 7/2001 | Kusumoto et al. | 323/355 |
| 2001/0039833 A1 | 11/2001 | Engel et al. | |
| 2002/0007685 A1 * | 1/2002 | Kunz et al. | 73/861.58 |
| 2002/0128543 A1 * | 9/2002 | Leonhardt | 600/316 |
| 2002/0138009 A1 * | 9/2002 | Brockway et al. | 600/485 |
| 2003/0216666 A1 * | 11/2003 | Ericson et al. | 600/561 |
| 2004/0000713 A1 * | 1/2004 | Yamashita et al. | 257/728 |
| 2004/0094303 A1 * | 5/2004 | Brockman et al. | 166/313 |
| 2004/0158294 A1 * | 8/2004 | Thompson | 607/17 |
| 2004/0182392 A1 * | 9/2004 | Gerder et al. | 128/204.22 |
| 2005/0081639 A1 * | 4/2005 | Gourlay | 73/718 |
| 2005/0107847 A1 * | 5/2005 | Gruber et al. | 607/61 |
| 2005/0204811 A1 * | 9/2005 | Neff | 73/204.11 |
| 2005/0246127 A1 * | 11/2005 | Renken et al. | 702/117 |
| 2005/0273014 A1 * | 12/2005 | Gianchandani et al. | 600/505 |
| 2005/0277839 A1 * | 12/2005 | Alderman et al. | 600/504 |
| 2006/0020239 A1 * | 1/2006 | Geiger et al. | 604/9 |
| 2006/0081067 A1 * | 4/2006 | Budmiger | 73/861.08 |
| 2007/0261496 A1 * | 11/2007 | Jonsson et al. | 73/723 |

FOREIGN PATENT DOCUMENTS

| | | |
|---|---|---|
| DE | 10133120 A1 * | 1/2003 |
| WO | WO 99/26530 | 6/1999 |
| WO | WO 01/12092 A1 | 2/2001 |
| WO | WO 2005/106401 | 11/2005 |

* cited by examiner

DEVICE FOR MEASURING A VOLUME FLOW WITH INDUCTIVE COUPLING

CROSS REFERENCE TO RELATED APPLICATIONS

This application claims the benefit of priority under 35 U.S.C. § 119 of German Patent Application DE 10 2005 008 698 filed Feb. 25, 2005, the entire contents of which are incorporated herein by reference.

FIELD OF THE INVENTION

The present invention pertains to a device for measuring a volume flow, especially to a tidal volume flow sensor, with a flow channel and with a sensor element arranged within the flow channel.

BACKGROUND OF THE INVENTION

A device for measuring a breathing gas volume flow is now present in practically all respirators (also known as ventilators). The so-called hot wire anemometry has proved to be an especially sensitive method for measuring the volume flow. A thin, so-called hot wire, whose resistance depends on the temperature, is arranged in the flow path of the gas of the hot wire anemometry measuring device. The hot wire is cooled by the flow depending on the intensity of the flow, so that the resistance of the wire at a defined current flowing through the wire is an indicator of the volume flow of the gas with which the gas is flowing past the wire. Hot wire anemometers are therefore preferably used because they themselves cause only a slight pressure loss within the flow channel. However, they have the drawback that the signal, which contains the information on the volume flow, is very weak.

A Wheatstone bridge circuit is frequently used for the analog evaluation of such a weak electric measured signal. The measuring element in the form of the hot wire is an element of the bridge circuit, but this measuring element is often not located in the immediate vicinity of the other elements of the bridge circuit. A cable connection is therefore necessary in these cases. The cable connection must, however, have a high-quality design in order to keep the resistance associated therewith as low as possible and as reproducible as possible.

Besides the problems concerning the cable connection, the coupling of the cables with the sensor (hot wire) itself is a source of additional possibilities of error, since the output signal may be directly affected by very low additional resistances, which may be caused, e.g., by welding and soldering resistances as well as cable and plug resistances. On the other hand, it is difficult to reach high reproducibility during welding or soldering operations. Thus, precisely these sources of additional resistance do represent a great problem when the change in the resistance of the hot wire is to be determined with precision.

In addition, the measured signal of a hot wire anemometer is affected not only by the volume flow but also by the absolute temperature of the gas flowing past and the composition of that gas.

It is known in this connection that the resistance of the hot wire and that of a temperature compensation wire are evaluated with a common bridge circuit during the measurement of the breathing gas volume flow. Both the hot wire and a second, unheated wire (temperature compensation wire), whose resistance is an indicator of the absolute temperature of the gas, are part of the bridge circuit in such a device.

If the direction of the gas flow is also to be determined besides the absolute value of the volume flow, it is necessary to also evaluate the signal of a second hot wire, in which case this second hot wire is arranged, unlike the first hot wire, in the shadow of a flow resistance such that a greatly reduced volume flow is admitted to the second hot wire when the flow takes place in a first direction, whereas this reduction does not take place in case of the opposite direction of flow. As a result, the direction of flow can be inferred from the measured cooling of the second hot wire compared to the first hot wire.

Thus, especially if the direction of flow of the gas is also to be measured, there will be a large number of connections between the measuring electronic unit, on the one hand, and sensors arranged in the flow channel, on the other hand, which are all subject to the above-mentioned problems of the undefined contact resistances, so that the entire measurement of the volume flow and of the direction of flow of the gas contains considerable sources of error. This problem is not limited to the use of hot wire anemometers, but it also occurs in the case of other electrically sensitive sensors for volume flow measurement in a flow channel.

SUMMARY OF THE INVENTION

The basic object of the present invention is therefore to provide a device for measuring a volume flow, in which the sensor signal, which is generated by sensor elements arranged in the flow channel, remains as free as possible from distortions during the transmission to an evaluating unit.

This object is accomplished according to the present invention by providing an internal circuit, which is arranged within the flow channel and comprises the sensor element; by providing an external circuit, which is arranged outside the flow channel, and by the external circuit being designed for contactless inductive coupling with the internal circuit for supplying same with energy and for reading it.

The solution according to the present invention with the inductive coupling between the internal circuit and the external circuit is associated with the advantage that no direct electric contact, for example, plug type connections or soldered connections, are necessary any longer. Contact resistances, which may also change during movement of the cables or in case of a change in the temperature of the contact points, cannot develop, either.

Via the external circuit, connected to an external electromagnetic field, electric power can be coupled into the internal circuit in the device according to the present invention and a hot wire with a temperature-dependent resistance, which is preferably present there, can thus be heated. As a result, this hot wire can assume a temperature above the gas temperature. If the volume flow of the gas that flows past the sensor element designed as a hot wire changes, the hot wire will be cooled differently and its resistance will change. The resonant frequency of the internal circuit, which forms an electric oscillatory circuit, will subsequently change. This detuning of the resonant frequency can be read by an operating electronic system and subsequently compensated in terms of automatic control technology by increasing or reducing the coupled-in electric power. This change in power, which can be measured, for example, by means of a current measurement, is, in turn, an indicator of how great the change in the temperature dissipation is in the internal circuit, and it is consequently an indicator of the volume flow.

In a preferred embodiment of the present invention, the internal circuit has a first inductive element and a first capacitive element. The resonant frequency of the internal circuit can then be adapted to the operating electronic system as well as to the volume flows used by dimensioning the inductance and the capacitance.

In another preferred manner, the capacitive element may be designed as a variable capacitive element and especially as a moisture sensor. As a result, the moisture content of the gas can also be determined, besides the volume flow of the gas, by means of the external circuit.

If the effect of the absolute gas temperature is also to be taken into account during the measurement of the volume flow, it is, furthermore, preferred to provide an internal temperature measuring circuit with a temperature sensor element in the flow channel. In a first alternative, the internal temperature measuring circuit is designed for the contactless, inductive coupling with the external circuit, which is linked with the advantage that only one common circuit is necessary for reading the internal circuit and the temperature measuring circuit. However, an external temperature measuring circuit, which is designed for the contactless, inductive coupling with the internal temperature measuring circuit, may also be provided in a second alternative. The absolute temperature of the gas can be measured independently from the volume flow in this case. Contacts with possibly varying resistances are avoided during the determination of the absolute temperature of the gas in both alternatives.

To make it also possible to correspondingly adapt the resonant frequency to the conditions of use in the internal temperature measuring circuit as well, this oscillatory circuit preferably has a second inductive element and a second capacitive element. In an especially preferred manner, the second capacitive element may likewise be designed as a moisture sensor. As a result, the moisture content of the gas can also be determined from the outside, besides its temperature.

A heating element is arranged in the flow channel in another preferred embodiment, and a flow resistance is provided between the heating element and the internal circuit, and the flow resistance is arranged in the flow channel such that the heating element and the flow resistance are located in the same area of the cross section of the flow channel. As a result, the heating element is "in the shadow" of the flow resistance in case the gas flows to the heating element past the flow resistance coming from the internal circuit. The volume flow occurring at the heating element is then reduced and the determination of the direction of flow can be performed in the above-described manner.

In an especially preferred manner, the flow resistance may be designed for this purpose as a projection in the wall of the flow channel, which is associated with a simple construction and leads to a low pressure loss through the flow resistance. On the other hand, the flow resistance may also be arranged in the center of the flow channel, which is associated with accurate measurement, even though it does require a more complicated design, because a greater effect is obtained in the middle of the channel on the basis of the higher velocity of flow prevailing there.

Furthermore, it is preferable for the external circuit to be connected detachably to the flow channel. This makes it possible to separate the flow channel with the internal circuit as well as the external circuit with the operating electronic unit. Combined with the inductive coupling, certain components are prevented in this manner from being needlessly exposed to stresses during cleaning.

Furthermore, the flow channel may be designed as a respiration tube and the external circuit arranged at a spaced location from the flow channel. This makes it possible to introduce the tube into the body of a patient, while the operating electronic unit with the external circuit is arranged outside the body. In particular, dead spaces, which would otherwise be necessary for the determination of the inspiratory and expiratory volume flow, are thus avoided in the respiration system. These dead spaces are formed due to the fact that the sensor elements would otherwise have to be provided in a part of the tube provided extra for this purpose outside the patient's body.

In an especially preferred manner, a second internal circuit, which is arranged at a spaced location from the first internal circuit in the respiration tube, can be provided next to the first internal circuit. As a result, the measurement of the direction of flow is made possible by measuring the time difference with which a change in temperature occurs at the two circuits.

The present invention will be explained below on the basis of a drawing showing exemplary embodiments, which are only preferred exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

DESCRIPTION OF THE PREFERRED EMBODIMENTS

Figure 1:
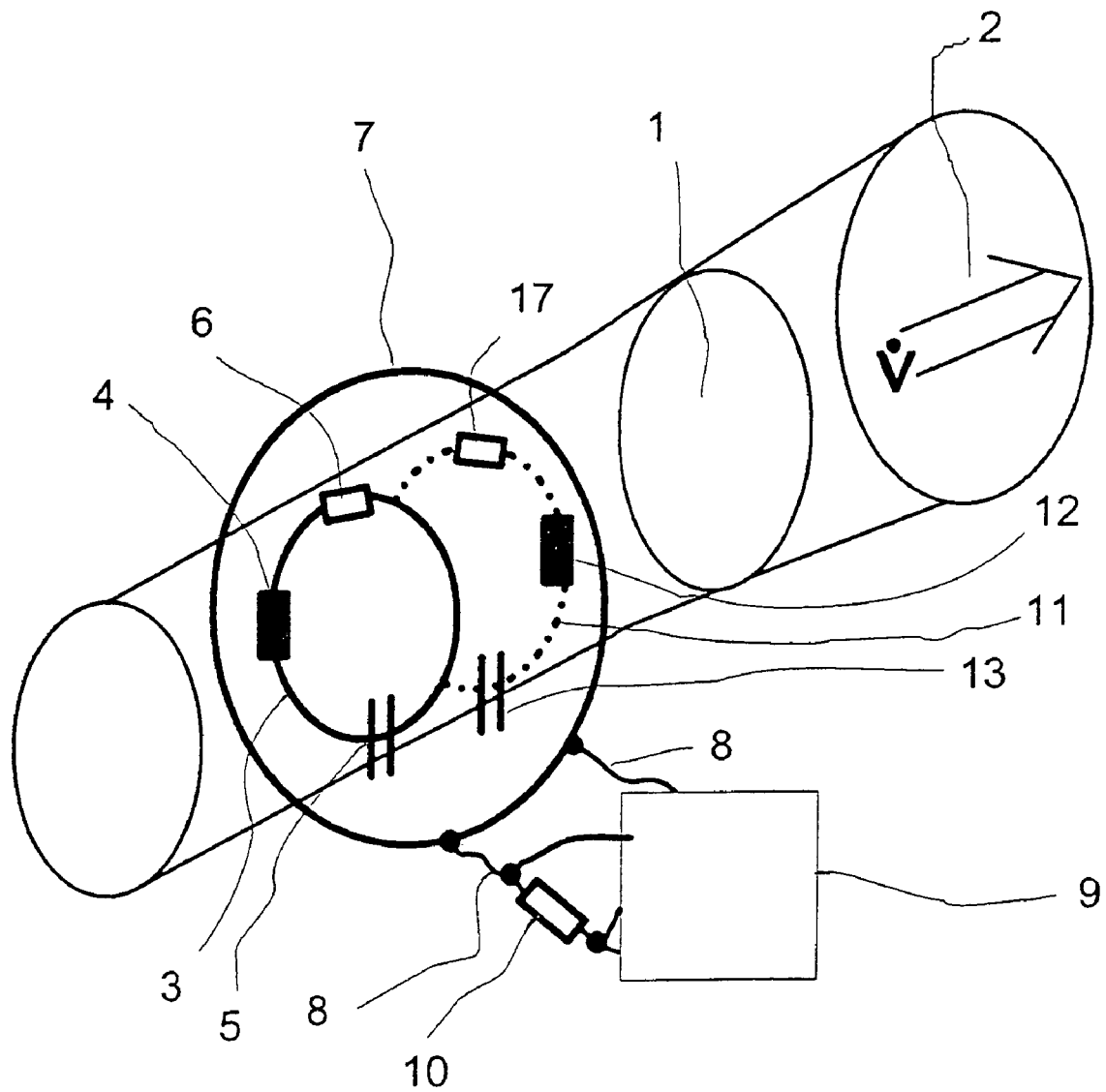
FIG. 1 is a first exemplary embodiment of a device according to the present invention for measuring a volume flow.

Referring to the drawings in particular, FIG. 1 shows a first exemplary embodiment of the device according to the present invention for measuring a volume flow, this exemplary embodiment, which is a preferred exemplary embodiment in this respect, being a tidal volume flow sensor. The device comprises a flow channel 1, through which a flow 2 of a gas passes, whose volume rate of flow (volume flow) $\dot{V}$ is to be determined.

The flow channel 1 has a circular cross section in this preferred exemplary embodiment, and an internal circuit 3 is arranged in the interior of the flow channel 1. The internal circuit 3 comprises a first inductive element 4, a first capacitive element 5 and a sensor element 6. The sensor element 6 is designed in a preferred manner as a hot wire for hot wire anemometry and has a temperature-dependent resistance. The first inductive element 4, the first capacitive element 5 and the sensor element 6 together form an electric oscillatory circuit, whose resonant frequency is obtained in the known manner from the capacitance C, the inductance L and the ohmic resistance $\Omega$ in the circuit. The resonant frequency of the oscillatory circuit can be adapted by appropriately dimensioning the inductance L and the capacitance C and selected in the process such that high sensitivity of the resonant frequency to changes in the resistance Ω of the sensor element 6 is guaranteed.

An external circuit 7 is arranged around the flow channel 1 in the area of the internal circuit 3, the external circuit being connected via feed lines 8 with an operating electronic unit 9. In addition, a flow-measuring resistor 10 is provided in one of the feed lines 8.

The external circuit 7 is designed for contactless, inductive coupling with the internal circuit 3 such that an electromagnetic field generated in the area of the external circuit 7 by the external circuit acts on the internal circuit 3 such that an electric power can be inductively transmitted from the external circuit 7 to the internal circuit 3. Thus, there is only an inductive connection between the external circuit 7 and the internal circuit 3 in the device according to the present invention, so that detachable connections, which would be associated with non-reproducible contact resistances, need not be provided or may optionally be provided in the device according to the present invention.

In addition, a temperature-measuring circuit 11, which comprises a temperature sensor element 17, which is preferably designed as a resistor wire, is provided in the flow channel 1 in the area of the external circuit 7 in this exemplary embodiment, which is a preferred embodiment in this respect. In addition, the temperature-measuring circuit 11 has a second inductive element 12 and a second capacitive element 13. The elements 12, 13 of the temperature-measuring circuit 11 may be dimensioned similarly to the internal circuit 3 in order to obtain a desired resonant frequency of the oscillatory circuit formed by these elements. The dimensioning (resonant frequency, quality, impedance) of the temperature-measuring circuit 11 may deviate from that of the internal circuit 3 to the extent that electric power released by the external circuit 7 is not absorbed by the temperature-measuring circuit 11.

Both the first capacitive element 5 and the second capacitive element 13 may be designed as variable elements in such a way that their capacitance depends on the moisture content of the gas, so that the capacitive elements 5, 13 can be used as moisture sensors. Thus, the moisture content of the gas can also be determined, if necessary, by means of the operating electronic unit 9, besides the volume flow and the absolute temperature.

Both the internal circuit 3 and the temperature-measuring circuit 11 are located in the area of the external circuit 7 in this exemplary embodiment, which is a preferred exemplary embodiment in this respect. Thus, the internal temperature-measuring circuit 11 is designed for contactless, inductive coupling with the external circuit 7, and both circuits 3, 11, located in the interior of the flow channel 1, can be evaluated by means of the common operating electronic unit 9.

During the measurement of the volume flow $\dot{V}$ with which the gas flows through the flow channel 1, the device according to the present invention preferably operates in the so-called constant-temperature anemometer mode. The hot wire provided in the internal circuit 3 is supplied for this purpose with such an amount of electric power that the hot wire has a resistance corresponding to the desired temperature. That the hot wire has this desired resistance can be determined in the operating electronic unit 9 from the fact that the oscillatory circuit formed by the internal circuit 3 has a corresponding resonant frequency. The electric power necessary for heating up is irradiated in the device according to the present invention via the inductive coupling between the internal circuit 3 and the external circuit 7, without a direct electric connection with detachable contacts being necessary.

If the volume flow $\dot{V}$ changes in the flow channel 1, the hot wire is cooled more or less intensely and the resistance of the hot wire changes, so that the resonant frequency or the quality of the oscillatory circuit and consequently the coupling with the external circuit 7 will change as well. To obtain the resonant frequency necessary for the desired temperature again, the electric power irradiated via the external circuit 7 is increased or decreased in order to set the adapted degree of coupling again, the power now irradiated being an indicator of the changed volume flow $\dot{V}$. The irradiated power is determined in this case from the voltage drop occurring over the flow-measuring resistor 10.

The absolute temperature of the gas flowing through the flow channel 1 is also taken into account during the determination of the volume flow $\dot{V}$ by evaluating the signal of the temperature-measuring circuit 11. The temperature-measuring circuit 11 is likewise a oscillatory circuit, so that its resonant frequency is an indicator of the temperature of the gas. The resonant frequency of the temperature-measuring circuit 11 is likewise determined by means of the operating electronic unit 9 connected to the external circuit 7 in the exemplary embodiment shown in FIG. 1, so that only a single evaluating electronic unit is necessary in this preferred exemplary embodiment. The second inductive element 12 and the second capacitive element 13 are dimensioned in this case such that no heating energy is introduced into the flow 2 by the temperature-measuring circuit 11. Only the resistance of the temperature sensor element 17 changes as a function of the gas temperature. This is also evaluated by the operating electronic unit 9 based on the coupling and the change of that coupling in the external circuit 7, as it was already described for the internal circuit 3. This signal is then included as an additional variable in the regulation of the internal circuit 3 in order to maintain the hot wire present in the internal circuit 3 at a constant excess temperature relative to the gas temperature.

It is also conceivable as an alternative that an additional external temperature-measuring circuit, via which the absolute temperature of the gas flowing through the flow channel 1 is determined, is also provided instead of only one external circuit 7. Determination of the absolute temperature independently from the internal circuit 3 is thus possible, but this determination can also be used to set a certain excess temperature relative to the gas temperature by means of the regulation.

Figure 2:
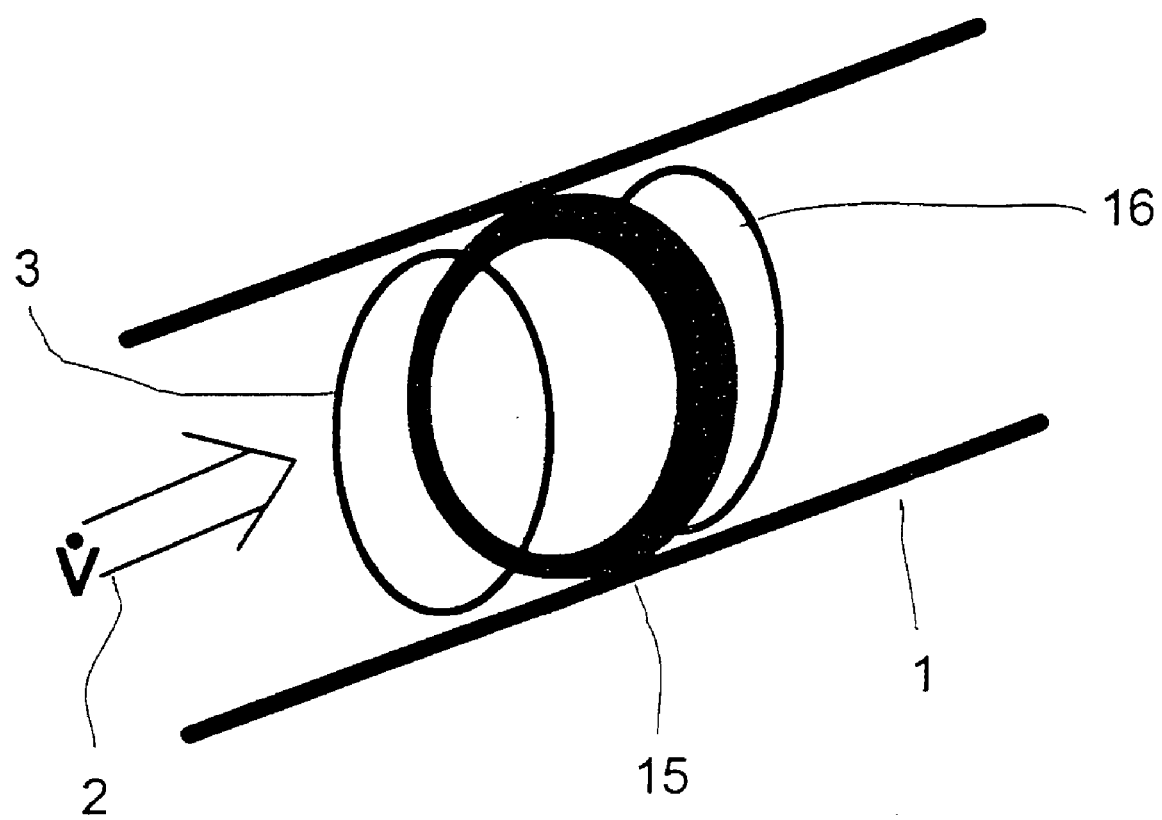
FIG. 2 is a second exemplary embodiment of a device according to the present invention.

FIG. 2 shows a second exemplary embodiment of a device according to the present invention, where components identical to those in the first exemplary embodiment are designated by the same reference numbers. A flow obstacle, that forms a flow resistance 15, and a heating element 16 are additionally provided in this exemplary embodiment in the flow channel 1 next to the internal circuit 3. The heating element 16 and the flow resistance 15 are arranged in the same area of the cross section of the flow channel 1, so that the heating element 16 is "in the shadow" of the flow obstacle 15, since the flow 2 flows, as in the case being shown, coming from the internal circuit 3, past the flow resistance 15 and to the heating element 16, so that the heating element 16 is hidden by the shadow of the flow resistance 15, and the volume flow that is admitted to the heating element 16 is reduced.

It is possible due to the provision of the heating element 16 to also determine the direction of the flow 2 besides the absolute value of the volume flow $\dot{V}$ of the flow 2. If the flow 2 takes place in the direction that is indicated by the arrow shown in FIG. 2, the cooling effect associated with it at the heating element 16 is weaker than at the internal circuit 3. If the flow 2 takes place in the opposite direction, the cooling effects measured at the internal circuit 3 and at the heating element 16 are similar. Thus, the direction of the flow 2 can also be determined by means of the heating element 16. In the exemplary embodiment shown in FIG. 2, which is a preferred exemplary embodiment to this extent, the flow resistance 15 is designed as a projection, which is formed in the wall of the flow channel 1. Such a design can be manufactured easily, on the one hand, and, on the other hand, it has the advantage that the flow resistance 15 causes only a small pressure loss within the flow channel 1.

Figure 3:
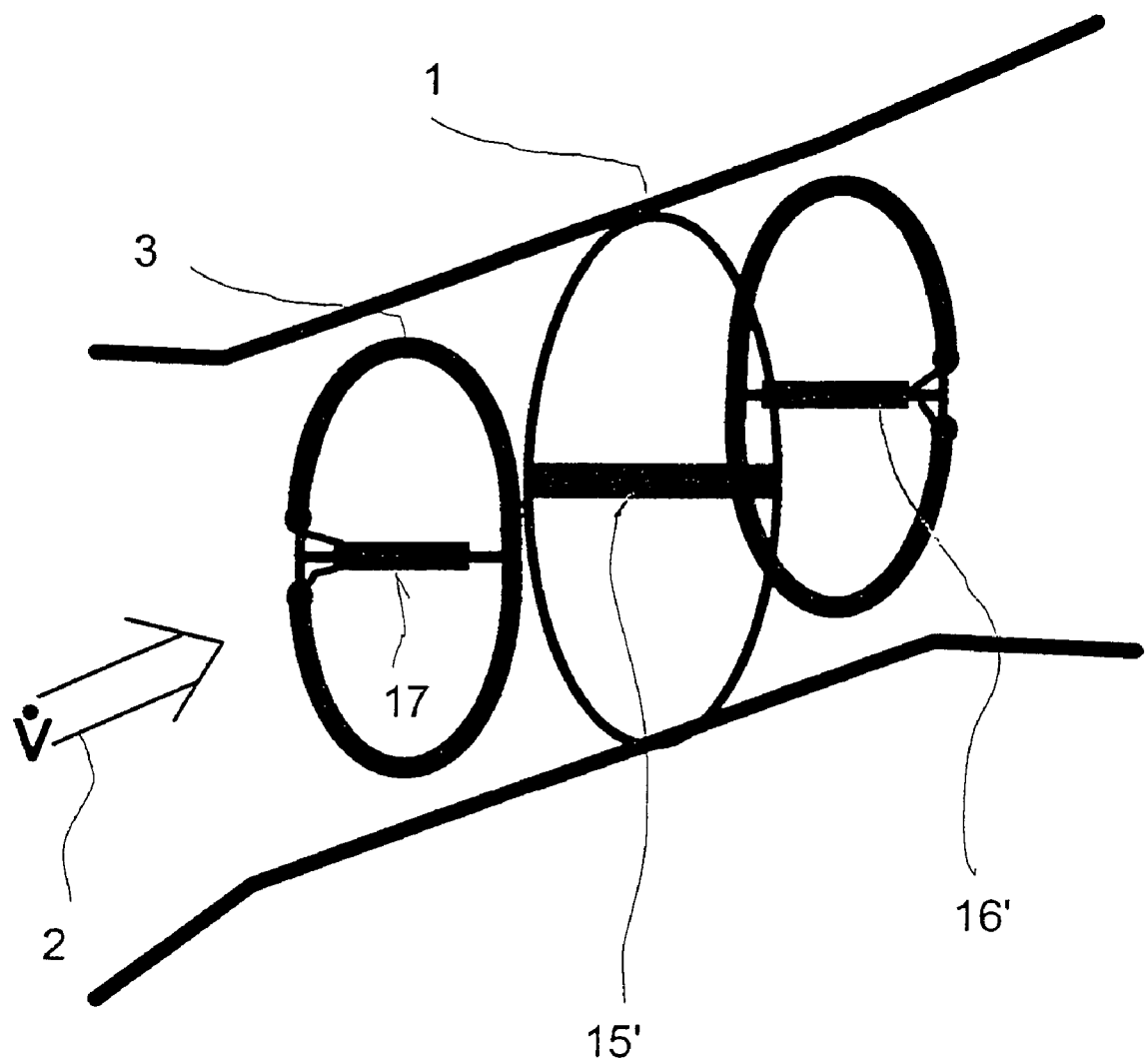
FIG. 3 is a third exemplary embodiment of a device according to the present invention.

As is shown in the exemplary embodiment shown in FIG. 3, the flow resistance 15' and the heating element 16' may be arranged, as an alternative to this, centrally in the cross section of the flow channel 1. Furthermore, the sensor element provided in the internal circuit 3 is preferably designed as a central web 17, which is arranged in parallel to the flow resistance 15', which is likewise provided centrally in the flow channel 1.

The determination of the direction of flow of the gas in the flow channel 1 is carried out in this third exemplary embodiment by means of the heating element 16' arranged centrally in the flow channel 1. This is associated with the advantage that the effect of the flow resistance on the heating element 16' is greater because of the higher velocity of flow prevailing in the center of the flow channel 1, but it has the drawback that the pressure loss caused hereby in the flow channel 1 is likewise greater as well.

Figure 6:
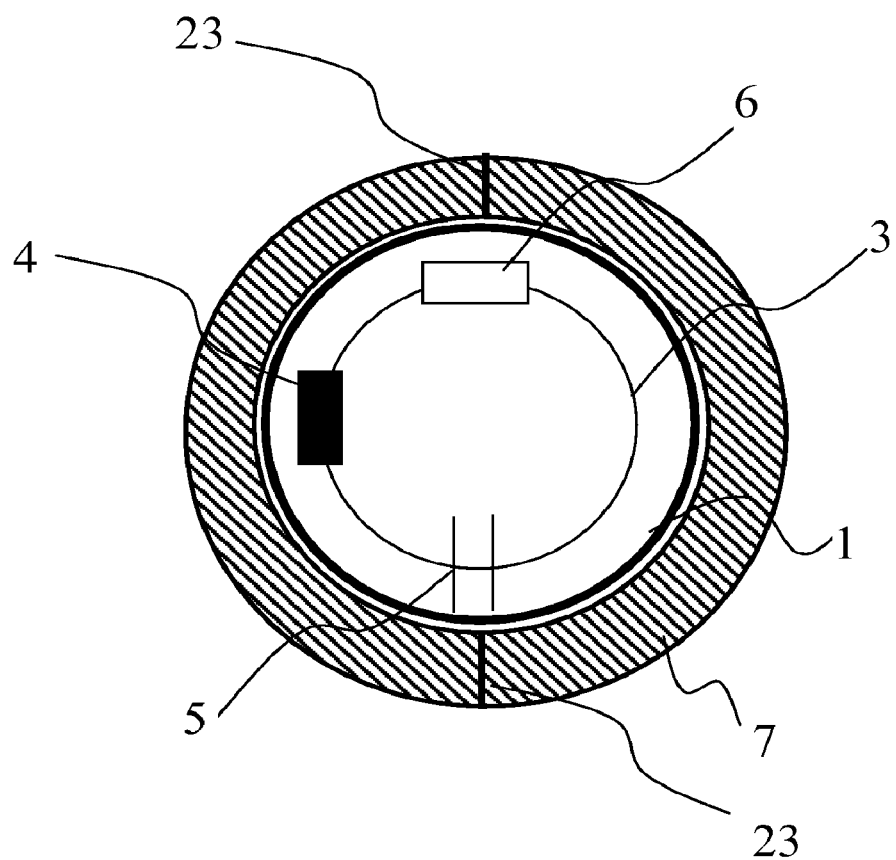
FIG. 6 is a cross sectional view of the first embodiment.

In a likewise preferred manner, as shown in FIG. 6, the external circuit 7 together with the operating electronic unit 9 may be detachably connected, by a connector 23, to the flow channel 1 in the exemplary embodiments shown so far, so that these two elements can be easily separated during the cleaning of the device. As a result, the external circuit 7 or the operating electronic unit 9 can be prevented from being damaged by cleaning agents.

Figure 4:
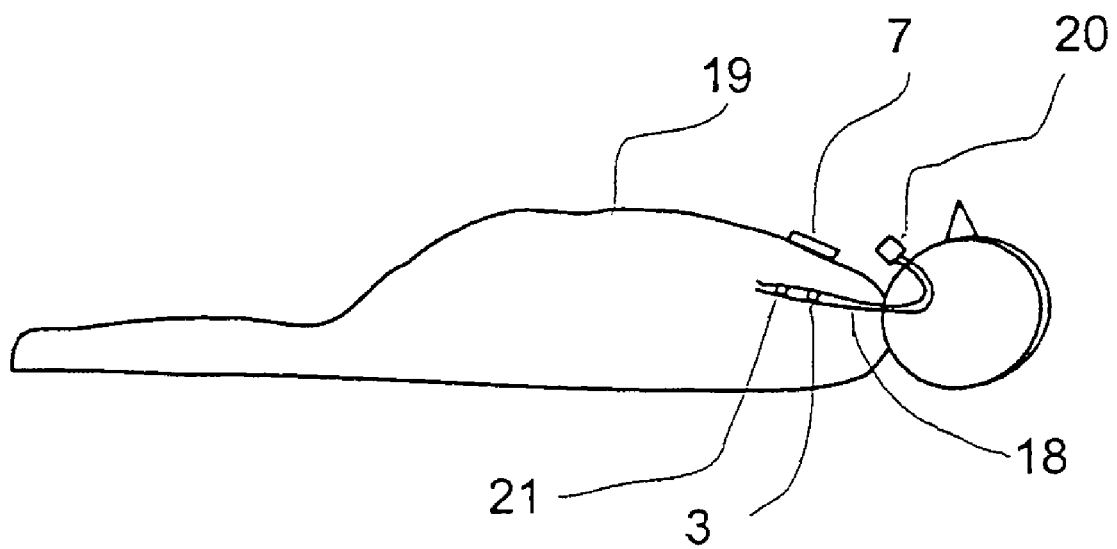
FIG. 4 is a fourth exemplary embodiment of a device according to the present invention.
Figure 5:
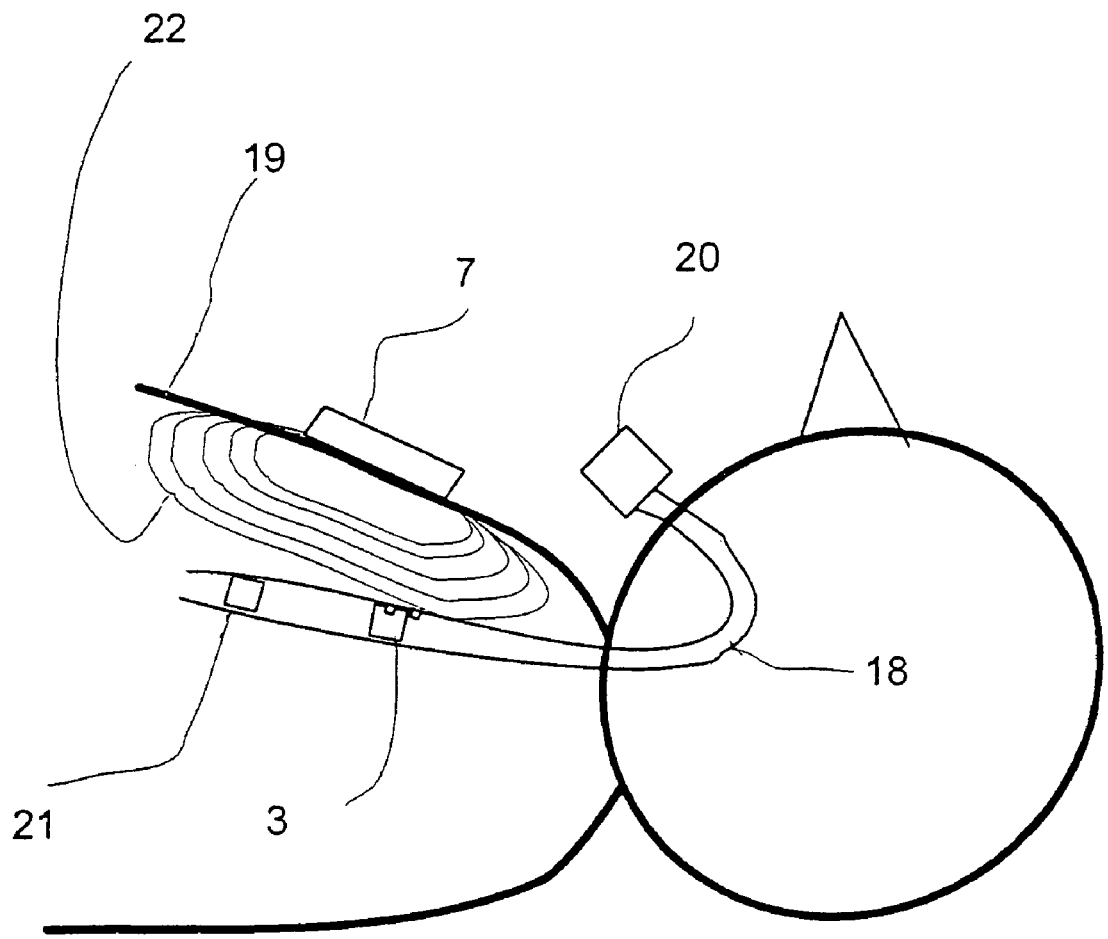
FIG. 5 is an enlarged view of the fourth exemplary embodiment.

FIG. 4 and FIG. 5 show a fourth exemplary embodiment of the present invention. The flow channel is designed as a respiration tube 18 for a patient 19 in this embodiment. Furthermore, the external circuit 7 is designed such that it can be arranged at a spaced location from the flow channel designed as a respiration tube 18. As a result, the part of the breathing air volume sensor arranged in the respiration tube 18 can be arranged in the patient's body. The respiration tube 18 has a tube connector 20, via which the respiration tube 18 can be connected to a respirator (not shown). Furthermore, an internal circuit 3 as well as a second internal circuit 21 are provided in the respiration tube 18. The direction of flow of the gas in the respiration tube 18 can be determined with the second internal circuit 21 together with the first internal circuit 3 by determining the time difference with which a change in the volume flow occurs at the two circuits 3, 21, the sign of the time difference indicating the direction of flow.

In addition, FIG. 5 shows the electromagnetic field 22, by means of which the electric power is irradiated into the circuits 3, 21, on the one hand, and, on the other hand, the particular resonant frequency of the circuits is set as a function of the particular volume flow by varying the irradiation of the power.

The problem of the variable contact resistances between the operating electronic unit 9, on the one hand, and circuits 3, 11 and 21 arranged in the flow, on the other hand, is avoided by means of the devices according to the present invention, which are shown in the exemplary embodiments, because these are coupled inductively with the operating electronic unit 9 by an electromagnetic field. In addition, it is possible with a device according to the present invention to arrange the internal circuits 3, 11 and 21 in the patient's body.

While specific embodiments of the invention have been shown and described in detail to illustrate the application of the principles of the invention, it will be understood that the invention may be embodied otherwise without departing from such principles.

What is claimed is:

1. A device for measuring a volume flow, the device comprising:
   a flow channel comprising a respiration tube;
   a sensor element comprising an internal circuit arranged within said flow channel, said internal circuit having an inductive element and a capacitive element;
   an external circuit arranged outside said flow channel at a spaced location from said respiration tube, said external circuit providing contactless inductive coupling with said internal circuit for supplying said internal circuit with energy and for sensor reading by detecting operation of said internal circuit, corresponding to fluid flow in said flow channel.

2. A device in accordance with claim 1, wherein said sensor element comprises a hot wire having a temperature-dependent resistance.

3. A device in accordance with claim 1, wherein said capacitive element is a variable capacitance element providing a moisture sensor.

4. A device in accordance with claim 1, further comprising an internal temperature-measuring circuit with a temperature sensor element, said internal temperature-measuring circuit being provided in said flow channel.

5. A device in accordance with claim 4, wherein said temperature sensor element is designed as a resistance wire.

6. A device in accordance with claim 4, wherein said internal temperature-measuring circuit provides contactless, inductive coupling with said external circuit for said sensor reading.

7. A device in accordance with claim 4, wherein said external circuit comprises an external temperature-measuring circuit for contactless, inductive coupling with said internal temperature-measuring circuit for sensor reading of said internal temperature-measuring circuit.

8. A device in accordance with claim 4, wherein said internal temperature-measuring circuit has an internal temperature-measuring circuit inductive element and an internal temperature-measuring circuit capacitive element.

9. A device in accordance with claim 8, wherein said internal temperature-measuring circuit capacitive element is designed as a variable element to provide a moisture sensor.

10. A device in accordance with claim 1, wherein said external circuit is detachably connected to said flow channel.

11. A device in accordance with claim 1, further comprising a second internal circuit arranged in said respiration tube at a spaced location from said internal circuit, said second internal circuit being designed for contactless, inductive coupling with said external circuit for energy supply from said external circuit to said second internal circuit and for sensor reading of said second internal circuit by said external circuit.

12. A device for measuring a volume flow, the device comprising:
   a flow channel;
   a sensor element comprising an internal circuit arranged within said flow channel;
   an external circuit arranged outside said flow channel, said external circuit providing contactless inductive coupling with said internal circuit for supplying said internal circuit with energy and for sensor reading including detecting operation of said internal circuit, corresponding to fluid flow in said flow channel;
a heating element arranged in said flow channel; and
a flow resistance arranged in said flow channel between said heating element and said internal circuit, said heating element and said flow resistance being arranged in a same cross sectional area of said flow channel.

13. A device in accordance with claim 12, wherein said flow resistance is designed as a projection in the wall of said flow channel.

14. A device in accordance with claim 12, wherein said cross sectional area of said flow channel heating element and said flow resistance is arranged centrally in said flow channel.

15. A device in accordance with claim 14, wherein said sensor element is disposed in a central region of said flow channel.

16. A volume flow measuring device comprising:
a respirator channel structure defining a fluid flow channel, said respirator channel structure defining an interior fluid flow region and an exterior surface;
a sensor element comprising an internal circuit arranged within said interior fluid flow region of said respirator channel structure, said internal circuit comprising a hot wire having a temperature-dependent resistance connected to a first inductive element and a first capacitive element to form an oscillatory circuit; and
an external circuit arranged at a spaced location from the exterior surface of said respirator channel structure, said external circuit providing contactless inductive coupling with said internal circuit for supplying said internal circuit with energy and for sensing changes in inductive coupling of said internal circuit with said external circuit corresponding to changes in fluid flow in said flow channel by sensing changes in said oscillatory circuit due to changes in resistance of said temperature-dependent resistance caused by changes in volume flow.

17. A device in accordance with claim 16, further comprising:
a heating element arranged in said flow channel; and
a flow resistance arranged in said flow channel between said heating element and said internal circuit, said heating element and said flow resistance being arranged in a same cross sectional area of said flow channel.

18. A flow attribute measuring device comprising:
a respirator tube defining a fluid flow channel, said respirator tube defining an interior fluid flow region and an exterior;
a sensor element comprising an internal circuit arranged within said flow channel interior, said internal circuit comprising a resistance connected to an inductive element and a capacitive element to form an oscillatory circuit; and
an external circuit arranged at the exterior of said flow channel such that said external circuit is at a spaced location from said flow channel of said respirator tube, said external circuit providing contactless inductive coupling with said internal circuit for supplying said internal circuit with energy and for sensing changes in inductive coupling of said internal circuit with said external circuit corresponding to changes in fluid attributes by sensing changes in said oscillatory circuit due to changes in one of said resistance and capacitive element caused by changes in flow attributes.

19. A device in accordance with claim 18, wherein said resistance is a temperature-dependent resistance.

20. A device in accordance with claim 18, wherein said resistance is a hot wire heated by supplying said internal circuit with energy, said hot wire having a temperature-dependent resistance to detect a volume rate of fluid flow in said flow channel.

21. A flow attribute measuring device comprising:
a channel structure defining a fluid flow channel, said channel structure defining an interior fluid flow region and an exterior;
a sensor element comprising an internal circuit arranged within said flow channel interior, said internal circuit comprising a resistance connected to an inductive element and a capacitive element to form an oscillatory circuit, said capacitive element being a variable capacitance element providing a moisture sensor; and
an external circuit arranged at the exterior of said flow channel, said external circuit providing contactless inductive coupling with said internal circuit for supplying said internal circuit with energy and for sensing changes in inductive coupling of said internal circuit with said external circuit corresponding to changes in fluid attributes by sensing changes in said oscillatory circuit due to changes in one of said resistance and capacitive element caused by changes in flow attributes.

22. A device for measuring a volume flow, the device comprising:
a flow channel comprising a respiration tube;
a sensor element comprising an internal circuit arranged within said flow channel;
an external circuit arranged outside said flow channel at a spaced location from said respiration tube, said external circuit providing contactless inductive coupling with said internal circuit for supplying said internal circuit with energy and for sensor reading by detecting operation of said internal circuit, corresponding to fluid flow in said flow channel, said external circuit being detachably connected to said flow channel.

* * * * *